US010351589B2

(12) United States Patent
Bäckström et al.

(10) Patent No.: US 10,351,589 B2
(45) Date of Patent: Jul. 16, 2019

(54) 3.ALPHA.-ETHYNYL, 3.BETA.-HYDROXY-5.ALPHA.-PREGNAN-20-OXIME FOR USE IN THE TREATMENT OF CNS DISORDERS

(71) Applicant: Umecrine Cognition AB, Solna (SE)

(72) Inventors: Torbjörn Bäckström, Umeå (SE); Gianna Ragagnin, Umeå (SE)

(73) Assignee: Umecrine Cognition AB, Solna (SE)

( * ) Notice: Subject to any disclaimer, the term of this patent is extended or adjusted under 35 U.S.C. 154(b) by 0 days.

(21) Appl. No.: 15/542,800

(22) PCT Filed: Jan. 11, 2016

(86) PCT No.: PCT/GB2016/050059
§ 371 (c)(1),
(2) Date: Jul. 11, 2017

(87) PCT Pub. No.: WO2016/113549
PCT Pub. Date: Jul. 21, 2016

(65) Prior Publication Data
US 2017/0369522 A1 Dec. 28, 2017

(30) Foreign Application Priority Data
Jan. 12, 2015 (SE) .................................... 1500018

(51) Int. Cl.
C07J 41/00 (2006.01)
A61K 31/57 (2006.01)
A61K 45/06 (2006.01)

(52) U.S. Cl.
CPC ............ *C07J 41/005* (2013.01); *A61K 31/57* (2013.01); *A61K 45/06* (2013.01); *Y02A 50/463* (2018.01)

(58) Field of Classification Search
CPC ................. C07J 41/005; A61K 31/27
See application file for complete search history.

(56) References Cited

U.S. PATENT DOCUMENTS

| | | | |
|---|---|---|---|
| 2,713,061 A | 7/1955 | Kathol | |
| 3,173,932 A | 3/1965 | Cantrall et al. | |
| 5,232,917 A | 8/1993 | Bolger et al. | |
| 5,925,630 A | 7/1999 | Upasani et al. | |
| 5,939,545 A | 8/1999 | Upasani et al. | |
| 6,143,736 A | 11/2000 | Upasani et al. | |
| 6,277,838 B1 | 8/2001 | Upasani et al. | |
| 6,596,885 B2 | 7/2003 | Claussner et al. | |
| 6,852,710 B2 | 2/2005 | Rao et al. | |
| 8,580,983 B2 | 11/2013 | Backstrom et al. | |
| 9,200,028 B2 | 12/2015 | Backstrom et al. | |
| 9,801,894 B2 | 10/2017 | Doverskog et al. | |
| 2004/0242549 A1 | 12/2004 | Covey et al. | |
| 2008/0119416 A1* | 5/2008 | Backstrom | C07J 1/00 514/26 |
| 2018/0015103 A1 | 1/2018 | Doverskog et al. | |

FOREIGN PATENT DOCUMENTS

| | | |
|---|---|---|
| FR | 1463755 A | 7/1966 |
| WO | 1994/27608 A1 | 12/1994 |
| WO | 1999/045931 A1 | 9/1999 |
| WO | 2003/047577 A2 | 6/2003 |
| WO | 03059357 A1 | 7/2003 |
| WO | 2006/056794 A1 | 6/2006 |
| WO | 2007/103162 A2 | 9/2007 |
| WO | 2008063128 A1 | 5/2008 |
| WO | 2008/155534 A2 | 12/2008 |

(Continued)

OTHER PUBLICATIONS

Wang, M.D., et al., "The Inhibitory Effects of Allopregnanolone and Pregnanolone on the Population Spike, Evoked in the Rat Hippocampal CA1 Stratum Pyramide in vitro, Can be Blocked Selectively by Epiallopregnanolone", Acta Physiol Scan, 169:333-341, 2000.
Wang, M., et al., "3Beta-Hydroxypregnane Steroids Are Pregnenolone Sulfate-Like GABAA Receptor Antagonists", The Journal of Neuroscience, 22(9):3366-3375, May 1, 2002.
Ahboucha, S., et al., "The Neurosteroid System: An Emerging Therapeutic Target for Hepatic Encephalopathy", Metab Brain Dis, 22:291-308, 2007.
Ahboucha et al., GABAergic neurosteroids: the "endogenous benzodiazepines" of acute liver failure. Neurochem Int. Jun. 2012;60(7):707-14.
Ahboucha et al., Increased levels of pregnenolone and its neuroactive metabolite allopregnanolone in autopsied brain tissue from cirrhotic patients who died in hepatic coma. Neurochem Int. Sep. 2006;49(4):372-8.

(Continued)

*Primary Examiner* — Susanna Moore
(74) *Attorney, Agent, or Firm* — McCarter & English, LLP; Xin Zhang; Steven G. Davis

(57) ABSTRACT

The invention relates to 3α-ethynyl, 3β-hydroxy, 5α-pregnan-20-oxime, represented by the following structural formula:

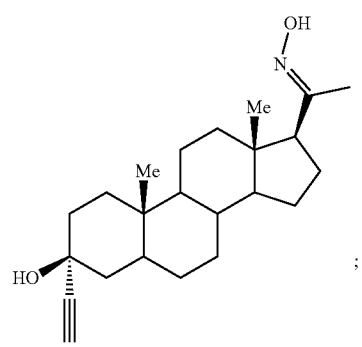

or a pharmaceutically acceptable salt thereof, which compounds and/or salts are useful as modulators of the mammal brain excitability via the gamma-aminobutyric acid receptor-chloride ionophore (GABA$_A$-R) complex and in the treatment of disorders such as hepatic encephalopathy, Down's syndrome and Alzheimer's disease.

8 Claims, No Drawings

(56) References Cited

FOREIGN PATENT DOCUMENTS

| WO | 2009142594 A1 | 11/2009 |
|---|---|---|
| WO | 2010/040020 A1 | 4/2010 |
| WO | 2010/144498 A2 | 12/2010 |
| WO | 2015/048818 A1 | 4/2015 |
| WO | 2015114308 A1 | 8/2015 |

OTHER PUBLICATIONS

Ahboucha et al., Indomethacin improves locomotor deficit and reduces brain concentrations of neuroinhibitory steroids in rats following portacaval anastomosis. Neurogastroenterol Motil. Aug. 2008;20(8):949-57.

Ahboucha et al., Neuroactive steroids and fatigue severity in patients with primary biliary cirrhosis and hepatitis C. Neurogastroenterol Motil. Jun. 2008;20(6):671-9.

Ahboucha et al., Reduced brain levels of DHEAS in hepatic coma patients: significance for increased GABAergic tone in hepatic encephalopathy. Neurochem Int. Jul. 2012;61(1):48-53.

Ahboucha et al., Role of endogenous benzodiazepine ligands and their GABA-A-associated receptors in hepatic encephalopathy. Metab Brain Dis. Dec. 2005;20(4):425-37.

Ahboucha et al., The neurosteroid system: implication in the pathophysiology of hepatic encephalopathy. Neurochem Int. Mar.-Apr. 2008;52(4-5):575-87.

Ahboucha et al., Unequivocal Evidence for a Role of Neurosteroids with Positive Allosteric Modulatory Properties at the GABA-A Receptor in the Pathogenesis of Hepatic Encephalopathy. Hepatology. Oct. 2003;38:178A, Abstract 48.

Bassett et al., Amelioration of hepatic encephalopathy by pharmacologic antagonism of the GABAA-benzodiazepine receptor complex in a rabbit model of fulminant hepatic failure. Gastroenterology. Nov. 1987;93(5):1069-77.

Cordoba et al., Characteristics, risk factors, and mortality of cirrhotic patients hospitalized for hepatic encephalopathy with and without acute-on-chronic liver failure (ACLF). J Hepatol. Feb. 2014;60(2):275-81.

Gonzalez-Usano et al., Pregnenolone sulfate restores the glutamate-nitric-oxide-cGMP pathway and extracellular GABA in cerebellum and learning and motor coordination in hyperammonemic rats. ACS Chem Neurosci. Feb. 19, 2014;5(2):100-5.

Johansson et al., GABAA receptor modulating steriod antagonists (GAMSA) are functional in vivo, Journal of Steroid Biochemistry & Molecular Biology. 2016;160:98-105.

Johansson et al., GR3027 antagonizes GABAA receptor-potentiating neurosteroids and restores spatial learning and motor coordination in rats with chronic hyperammonemia and hepatic encephalopathy. Am J Physiol Gastrointest Liver Physiol. Sep. 1, 2015;309(5):G400-9.

Prakash et al., Mechanisms, diagnosis and management of hepatic encephalopathy. Nat Rev Gastroenterol Hepatol. Sep. 2010;7(9):515-25.

Umecrine Cognition, Umecrine Cognition announces positive topline Phase 1 data with GR3027 in hepatic encephalopathy demonstrating safety, tolerability and CNS target engagement. Press Release, 2 pages, Nov. 3, 2016.

Umecrine Cognition, Umecrine Cognition announces the publication of preclinical results of the candidate drug GR3027 aimed for the treatment of hepatic encephalopathy. Press Release, 1 page, Aug. 19, 2015.

Kanzo et al., Steroid compound used to treat hepatic encephalopathy, Acta Hepatologica Japonica. 2002;43(2);77-83.

* cited by examiner

3.ALPHA.-ETHYNYL, 3.BETA.-HYDROXY-5.ALPHA.-PREGNAN-20-OXIME FOR USE IN THE TREATMENT OF CNS DISORDERS

RELATED APPLICATION INFORMATION

This application is a 35 U.S.C. § 371 national stage filing of International Application No. PCT/GB2016/050059, filed on Jan. 11, 2016, which claims the benefit of Swedish Patent Application No. 1500018-5, filed on Jan. 12, 2015. The contents of each of the foregoing applications are incorporated herein by reference in their entirety.

FIELD OF THE INVENTION

This invention relates to a novel steroidal compound and its use in therapy, such as in the treatment of hepatic encephalopathy, Down's syndrome, Alzheimer's disease and cognitive impairment generally, as well as to pharmaceutical compositions comprising that compound. The invention also relates to the use of a known steroidal compound in the treatment of hepatic encephalopathy, Down's syndrome and Alzheimer's disease.

BACKGROUND OF THE INVENTION

The listing or discussion of an apparently prior-published document in this specification should not necessarily be taken as an acknowledgement that the document is part of the state of the art or is common general knowledge.

Metabolites of endogenous steroid hormones, such as the pregnanolones (including pregnenolone, progesterone, deoxycorticosterone, cortisone and cortisol), testosterone, androstenedione and dehydroepiandrosterone, have been the subject of various studies.

Many examples of 3-alpha-hydroxy-5-alpha/beta-steroids are known to act on the gamma-aminobutyric acid receptor-chloride ionophore ($GABA_A$-R) complex and are therefore referred to as $GABA_A$ receptor modulating steroids (GAMS). Mechanisms of interaction at the receptor site have not yet been fully elucidated, due to the structural complexity of the $GABA_A$-R complex. However, the GABA receptor family includes several subunit components, some of which are known to be related to specific functions and disorders of the CNS.

3-alpha-hydroxy-5-alpha/beta-steroids are produced in high amounts over several days/week, and can directly cause inhibition of CNS functions. Examples of disorders and symptoms caused by the direct action of 3-alpha-hydroxy-5-alpha/beta-steroids include premenstrual dysphoric disorder, premenstrual syndrome, dementia, Alzheimer's disease, Down's syndrome, sedation, tiredness, chronic fatigue syndrome, memory disturbance, learning disturbance, disturbance of motor function, fractures, clumsiness, increased appetite and food cravings, obesity, relapse in alcohol or substance abuse, negative mood as tension, irritability, depression, decreased hearing and eye sight, worsening of Petit Mal epilepsy and burn out syndrome.

Continuous and/or long-term exposure to 3-alpha-hydroxy-5-alpha/beta-steroids causes tolerance to develop in the $GABA_A$ receptor system. This tolerance is the first step in a process that may ultimately lead to stress sensitivity, concentration difficulties, and loss of impulse control and depression. Further, the action of 3-alpha-hydroxy-5-alpha/beta-steroids has been found to be a factor that reinforces drug dependency.

Continuous but shorter-term exposure on the other hand results in a withdrawal effect when exposure is terminated. This phenomenon occurs e.g. during menstruation, when the production of 3-alpha-hydroxy-5-alpha/beta-steroids by the corpus luteum of the ovary is interrupted. This withdrawal phenomenon also occurs after giving birth when their production by the placenta is interrupted, or at the end of a period of stress (adrenal glands produce 3-alpha-hydroxy-5-alpha/beta-steroids during stress).

Examples of conditions that are influenced by this such withdrawal and/or abstinence include partial epilepsy, "catamenial epilepsy", migraine, mood changes and "weekend" headache.

The $GABA_A$ receptor is a chloride channel and exerts its action by changing the influx of chloride through the channel. It is known in the art that the neuronal activity in the brain is decreased when the $GABA_A$ receptor is open and large amounts of chloride ion flux into the cell. It is also known that there is a relationship between the amount of chloride moving in, and the clinical effect of a $GABA_A$ receptor active drug.

Benzodiazepines, barbiturates and, to an extent, alcohol exerts their action via this mechanism. This, however, also accounts for the adverse effects of these drugs.

A problem with the $GABA_A$ receptor is that it exerts its action in most parts of the brain. In view of this, complete blockers of GABA action are dangerous and may cause psychotic symptoms and convulsions. That said, when the action of 3-alpha hydroxy-5-alpha/beta-pregnan-steroids is to be antagonized it would be desirable to use compounds that specifically antagonize 3-alpha-hydroxy-5-alpha/beta-pregnan-steroid effects, whilst not antagonizing GABA's own effect.

Accordingly, the present invention endeavours to solve the problem of provision of specific agents that are capable of blocking GABA receptors, which compounds may thus be useful in the treatment of anomalies in the excitation of GABA receptors or other neurotransmitters related to GABA receptors.

International patent application WO 2008/063128 disclose 3-alpha-hydroxy steroids and 3-beta-hydroxy steroids. International patent application WO 99/45931 discloses antagonistic effects of the steroid 3-beta-OH-5alpha-pregnan-20-one. International patent application WO 03/059357 discloses 3-beta-hydroxy steroids and their antagonistic effect on the $GABA_A$ receptor.

U.S. Pat. Nos. 5,232,917, 5,925,630, 5,939,545, 6,143,736 and 6,277,838 disclose 3-alpha-hydroxy steroids and 3-beta-hydroxy steroids as agonistic modulators of the $GABA_A$ receptor with a specific focus on 3-alpha-hydroxy steroids and their benzodiazepine like effect. In US patent application US 2004/0242549, a number of steroids are disclosed.

The antagonistic effect of 3-beta-OH-5-alpha-pregnan-20-one and other 3-beta-OH—5-alpha/beta pregnan-steroids is discussed by Wang et al (*Acta Physiol. Scand.*, 169, 334 (2000) and *J. Neurosci.*, 22, 3366 (2002)).

Prior art compounds including those mentioned above are not specific to certain $GABA_A$-R subtypes. Accordingly, there is a need for compounds that are more selective to receptor sub-types.

Additionally prior art and naturally occurring steroids are subject to metabolism, are often not suitable for oral administration, and typically have poor permeability.

This makes it very difficult to administer such compounds. Accordingly, there is also a need for compounds that are less easily metabolized/degraded in the body, and/or have an improved permeability/bioavailability.

DESCRIPTION OF THE INVENTION

We have found that the compound 3α-ethynyl, 3β-hydroxy, 5α-pregnan-20-oxime may act as an antagonist to the $GABA_A$ receptor, and that it may do so by modulating steroid enhancement of the $GABA_A$-R complex, for example by modulating GAMS signaling effect as an antagonist of the GABA receptor subunit alpha 5.

According to the invention, there is provided the compound 3α-ethynyl, 3β-hydroxy, 5α-pregnan-20-oxime, or a pharmaceutically acceptable salt thereof, which compound and salts are referred to hereinafter together as "the compounds of the invention".

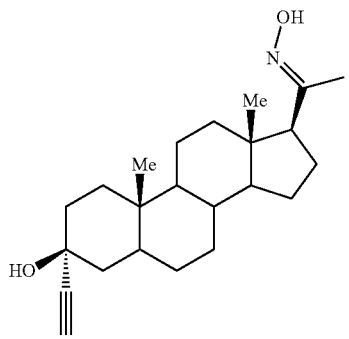 [SMILES: C#C[C@]1(O)CC[C@@]2(C)C(CCC3C2CC[C@@]2(C)C3CC[C@@H]2/C(C)=N/O)C1]

Pharmaceutically-acceptable salts include acid addition salts and base addition salts.

Such acid addition salts and base addition salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

Examples of acid addition salts that may be mentioned include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxybenzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), hydrohalide salts (e.g. hydrochloride, hydrobromide or hydroiodide salts), sulfonate salts (e.g. benzenesulfonate, methyl-, bromo- or chloro-benzenesulfonate, xylenesulfonate, methanesulfonate, ethanesulfonate, propanesulfonate, hydroxyethanesulfonate, 1- or 2-naphthalene-sulfonate or 1,5-naphthalene-disulfonate salts) or sulfate, pyrosulfate, bisulfate, sulfite, bisulfite, phosphate, monohydrogenphosphate, dihydrogenphosphate, metaphosphate, pyrophosphate or nitrate salts, and the like.

Examples of base addition salts that may be mentioned include salts formed with acids, such as HCl, alkali metals (such as Na and K salts), alkaline earth metals (such as Mg and Ca salts), organic bases (such as ethanolamine, diethanolamine, triethanolamine, tromethamine and lysine) and inorganic bases (such as ammonia and aluminium hydroxide). More particularly, base addition salts that may be mentioned include Mg, Ca and, more particularly, K, and, most particularly, Na salts.

In accordance with an aspect of the invention, there is provided 3α-ethynyl, 3β-hydroxy, 5α-pregnan-20-oxime hydrochloride salt. In accordance with a further aspect of the invention, there is provided 3α-ethynyl, 3β-hydroxy, 5α-pregnan-20-oxime sodium salt.

Compounds of the invention may be prepared for example as described hereinafter.

Medical and Pharmaceutical Uses

Compounds of the invention are indicated as pharmaceuticals. Therefore, according to a further aspect of the invention there is provided a compound as hereinbefore defined, for use as a pharmaceutical and/or for use in therapy, such as in medicine.

As described hereinafter, it has surprisingly been shown that compounds of the invention may enhance the effect of GABA in $GABA_A$ receptors containing the subunit composition α1,β2,γ2, whilst having no direct effect itself on chloride flux when applied alone on the $GABA_A$ receptor containing α1,β2,γ2.

In particular, it is been found that compounds of the invention may enhance the effect of GABA on α1,β2,γ2 receptors while at the same time being an antagonist to α5,β3,γ2 receptors. Surprisingly, simultaneous treatment with a 3-alpha-hydroxy-pregnan-steroids and compounds of the invention inhibits chloride flux through the human $GABA_A$ receptor of the alpha 5 type when recombinantly expressed in HEK-cells (Human embryonic kidney, HEK) induced by the 3-alpha-hydroxy-pregnan-steroid, but have low effect on chloride flux induced by GABA alone.

It has further been found that this action may be achieved at pharmacologically and physiologically suitable concentrations.

Accordingly, because compounds of the invention may block the action of 3-alpha-hydroxy-pregnan-steroids on the human $GABA_A$ receptor, they are potentially useful in the treatment of steroid-related CNS disorders, typically in human subjects.

"Steroid-related CNS disorders" include epilepsy, menstruation cycle dependent epilepsy, depression, stress related depression, migraine, tiredness and in particular stress related tiredness, premenstrual syndrome, premenstrual dysphoric disorder, menstrual cycle linked mood changes, cognitive impairment (including minimal cognitive impairment), menstrual cycle linked memory changes, stress related memory changes, stress related learning difficulties, hepatic encephalopathy, Down's syndrome, Alzheimer's disease, menstrual cycle linked difficulties in concentration, menstrual cycle linked sleep disorders and tiredness. There are also strong indications that also obesities and increased appetite, as well as relapses into alcohol and/or substance abuse, some forms of balance disturbances/disorders, moment disorders and co-ordination difficulties are steroid related or steroid induced, and "steroid-related CNS disorders" thus also include increased appetite, overeating and obesity, relapse of alcohol and substance abuse. The present invention thus offers compounds and methods for treatment, alleviation or prevention of these conditions.

Disorders that may be mentioned specifically include Down's syndrome and Alzheimer's disease and, especially, hepatic encephalopathy.

Hepatic encephalopathy disorders may be manifest and/or characterized by symptoms including impairment of one or more of the sleep-wake cycle, cognition, memory, learning, motor coordination and/or consciousness, as well as decreased energy levels, personality change, cognitive impairment, disorientation and/or coma and includes Type A hepatic encephalopathy, Type B hepatic encephalopathy, Type C hepatic encephalopathy, minimal hepatic encephalopathy, and overt, hepatic encephalopathy.

"Type A hepatic encephalopathy" typically refers to hepatic encephalopathy associated with acute liver failure, typically associated with cerebral oedema.

"Type B hepatic encephalopathy" typically refers to hepatic encephalopathy (bypass) caused by portal-systemic shunting without associated intrinsic liver disease.

"Type C hepatic encephalopathy" typically refers to hepatic encephalopathy occurring in patients with cirrhosis. This type is often subdivided into "episodic", "persistent" and "minimal" hepatic encephalopathy.

"Minimal hepatic encephalopathy" typically refers to hepatic encephalopathy that does not lead to clinically overt cognitive dysfunction, but can be demonstrated with neuropsychological studies.

"Overt hepatic encephalopathy" typically refers to clinically apparent hepatic encephalopathy manifest as neuropsychiatric syndrome with a large spectrum of mental and motor disorders. Overt hepatic encephalopathy may arise episodically, over a period of hours or days in patients that are previously stable or patients may presented with persistent neuropsychiatric abnormalities.

In addition to the above, although most liver transplant operations use livers from otherwise-healthy deceased donors, livers may also come from a living donor (a portion of a healthy person's liver). Patients with e.g. cirrhosis commonly experience hepatic encephalopathy and pre-operative hepatic encephalopathy, which is a significant predictor of post-transplant neurologic complications. Treatment of hepatic encephalopathy in patients about to undergo a liver transplant are included within the scope of the invention.

The term "hyperammonemia" typically refers to a metabolic disturbance characterized by an access of ammonia in the blood.

The term "acute on chronic liver failure" typically refers to acute decompensation of cirrhosis, at least one organ failure, or belongs to a sub-group with high short-term mortality rate.

The term "decompensated cirrhosis" is typically meant to include advanced liver cirrhosis with a range of clinical evidence such as jaundice, ascites, oedema, hepatic encephalopathy, gastrointestinal haemorrhage, portal hypertension, bacterial infections, or any combination thereof. It is to be contrasted with "compensated cirrhosis", which typically refers to liver cirrhosis without any clinical evidence but may include asymptotic esophageal or gastric varices and early symptoms such as fatigue and loss of energy, loss of appetite and weight loss, nausea or abdominal pain.

The term "portal hypertension" typically refers to a hepatic venous pressure gradient following liver cirrhosis, with or without associated transjugular intrahepatic portsystemic shunt (TIPS).

Compounds of the invention are indicated both in the therapeutic and/or prophylactic treatment of all of the above-mentioned conditions.

According to a further aspect of the present invention, there is provided a method of treatment of a steroid-related CNS disorder as hereinbefore mentioned, which method comprising administering a pharmaceutically effective amount of a compound of the invention to a patient in need of such treatment.

There is further provided a method for the treatment and/or prevention of steroid-related or steroid-induced memory and learning disorders, cognitive impairment, dementia and/or mood disorders, such as those described above by administering a compound of the invention to a patient in need thereof.

Compounds of the invention may have the advantage that they may prevent tolerance development and/or down-regulation of the $GABA_A$ receptor. Compounds of the invention may have the advantage that they may hinder withdrawal effects once steroid is withdrawn. In this way, compounds of the invention may have the advantage that they may preserve the sensitivity of the $GABA_A$ system and inhibit the development of a less sensitive state during the luteal phase of, for example, the menstrual cycle, so preventing symptoms such as migraine and/or epileptic seizures.

Another embodiment of the present invention is accordingly a method for treatment or prevention of steroid-tolerance development conditions or symptoms and/or of steroid-withdrawal conditions or symptoms, by administration of a compound of the invention to a patient in need thereof.

Examples of such symptoms and/or conditions that may be mentioned include sedation, tiredness, memory disturbance, learning disturbance, disturbance of motor function, clumsiness, e.g. symptoms in hepatic encephalopathy, increased appetite and food cravings, relapses in alcohol or substance abuse, negative mood as tension, irritability and depression which are the cardinal symptoms in the premenstrual syndrome and the worsening of Petit Mal epilepsy.

Conditions and symptoms caused by tolerance development after longer timeframes (e.g. several days) exposure to 3-alpha-hydroxy-5-alpha/beta-steroids are e.g. stress sensitivity, concentration difficulties, stress or menstrual cycle linked difficulties in concentration, sleep disorders, tiredness, loss of impulse control and depression, memory and learning disturbance. 3-alpha-hydroxy-5-alpha/beta-steroids also reinforce drug dependency. According to the present invention, these conditions or symptoms can be prevented, alleviated or treated by the administration of a compound of the invention to a patient in need thereof.

A continuous but shorter exposure to 3-alpha-hydroxy-5-alpha/beta-steroids gives a withdrawal effect when the exposure is ended. This phenomenon occurs during menstruation when the production of 3-alpha-hydroxy-5-alpha/beta-steroids by the corpus luteum of the ovary is interrupted. This withdrawal phenomenon also occurs after giving birth (post partum) when the 3-alpha-hydroxy-5-alpha/beta-steroid production by the placenta is interrupted. The same phenomenon is also noted when a period of stress is ended and the 3-alpha-hydroxy-5-alpha/beta-steroids produced by the adrenal during the stress are interrupted. Examples of conditions that are influenced by this withdrawal/abstinence phenomenon are partial epilepsy where the patient has an epileptic focus in the cerebral cortex where a worsening occurs at the withdrawal period during menstruation. This phenomenon is called "catamenial epilepsy". Other examples are menstrual related migraine and stress related migraine and mood changes post partum. Withdrawal phenomenon is a sign of an earlier developed tolerance.

One embodiment of the invention, addressing a problem afflicting numerous women, is a method for the treatment and/or prevention of side effects of anti-inflammatory steroid and postmenopausal therapy in human patients. According to the invention, these conditions or symptoms can be prevented, alleviated or treated by the administration of a compound of the invention to a patient in need thereof.

Another embodiment of the invention is the treatment and/or prevention of side effects of oral contraceptives in human patients. According to the invention, these conditions or symptoms can be prevented, alleviated or treated by the administration of a compound of the invention to a patient in need thereof. In this context, compounds of the invention may be administered together with the oral contraceptive, which may already be being taken by the patient. Nasal and percutaneous administrations are also suitable routes of administration.

In other words, compounds of the invention may act to treat stress-related and/or stress-induced conditions brought on by one or more of the three possible mechanisms by which steroids act on the central nervous system: namely by way of:
(a) direct action,
(b) tolerance induction, and/or
(c) withdrawal effect.

Further, within the scope of the above embodiment, doses of compounds of the invention may be adjusted to the levels of endogenous steroids during stress or the menstrual period.

"Patients" include mammalian (and especially human) patients.

The term "effective amount" refers to an amount of a compound, which confers a therapeutic effect on the treated patient. The effect may be objective (i.e. measurable by some test or marker) or subjective (i.e. the subject gives an indication of or feels an effect).

Compounds of the invention will normally be administered orally, intravenously, subcutaneously, buccally, rectally, dermally (e.g. percutaneously), nasally, tracheally, bronchially, sublingually, by any other parenteral route or via inhalation, in a pharmaceutically acceptable dosage form.

Compounds of the invention may be administered in the form of tablets, capsules or elixirs for oral administration, suppositories for rectal administration, sterile solutions or suspensions for parenteral, including intravenous or intramuscular administration, and the like.

The formulation of compositions comprising compounds of the invention may be adapted or adjusted according to normal pharmacological procedures, in a chemical form suitable for the chosen route, together with suitable adjuvants, carriers, diluents and vehicles, conventionally used and well-known to a person skilled in the art. Such formulations may thus be prepared in accordance with standard and/or accepted pharmaceutical practice.

According to a further aspect of the invention there is thus provided a pharmaceutical formulation including a compound of the invention, as hereinbefore defined, in admixture with a pharmaceutically acceptable adjuvant, diluent or carrier.

Depending on e.g. potency and physical characteristics of the compound of the invention (i.e. active ingredient), pharmaceutical formulations that may be mentioned include those in which the active ingredient is present in at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The invention further provides a process for the preparation of a pharmaceutical formulation, as hereinbefore defined, which process comprises bringing into association a compound of the invention, as hereinbefore defined with a pharmaceutically-acceptable adjuvant, diluent or carrier.

Compounds of the invention may also be combined with other therapeutic agents that are useful in one or more of:
(a) the treatment of a steroid-related CNS disorder;
(b) the treatment of a condition or a symptoms caused by tolerance development after exposure to 3-alpha-hydroxy-5-alpha/beta-steroids;
(c) the treatment of a condition that is influenced by withdrawal/abstinence of exposure to 3-alpha-hydroxy-5-alpha/beta-steroids;
(d) the treatment of one or more side effect of an anti-inflammatory steroid;
(e) the treatment of one or more side effect of postmenopausal therapy; and/or
(f) the treatment of one or more side effect of an oral contraceptive, or with an oral contraceptive per se. Such therapeutic agents, or oral contraceptives, are referred to hereinafter together as other or another "therapeutic agent(s) as hereinbefore defined".

For example, compounds of the invention may be included in a formulation or treatment regimen along with an oral contraceptive in order to alleviate and/or remove:
(i) the side effects of oral contraceptives; and/or
(ii) any unwanted effect of the periodical changes in endogenous steroids.

Further aspects of the invention provide for pharmaceutical compositions and kits of parts comprising therapeutically-suitable doses of other therapeutic agents as hereinbefore defined, in combination with a therapeutically suitable dose of a compound of the invention.

According to a further aspect of the invention, there is provided a combination product comprising:
(A) a compound of the invention, as hereinbefore defined; and
(B) at least one other therapeutic agent as hereinbefore defined,
wherein each of components (A) and (B) is formulated in admixture with a pharmaceutically-acceptable adjuvant, diluent or carrier.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:
(1) a pharmaceutical formulation including a compound of the invention, as hereinbefore defined, at least one other therapeutic agent as hereinbefore defined, and a pharmaceutically-acceptable adjuvant, diluent or carrier; and
(2) a kit of parts comprising components:
(a) a pharmaceutical formulation including a compound of the invention, as hereinbefore defined, in admixture with a pharmaceutically-acceptable adjuvant, diluent or carrier; and (b) a pharmaceutical formulation including at least one other therapeutic agent as hereinbefore defined in admixture with a pharmaceutically-acceptable adjuvant, diluent or carrier, which components (a) and (b) are each provided in a form that is suitable for administration in conjunction with the other.

The invention further provides a process for the preparation of a combination product as hereinbefore defined, which process comprises bringing into association a compound of the invention, as hereinbefore defined, with the at least one other therapeutic agent as hereinbefore defined, and at least one pharmaceutically-acceptable adjuvant, diluent or carrier.

By "bringing into association", we mean that the two components are rendered suitable for administration in conjunction with each other. Compounds of the invention may be employed as part of "add on therapy" in treatment involving the at least one other therapeutic agent as hereinbefore defined.

Thus, in relation to the process for the preparation of a kit of parts as hereinbefore defined, by bringing the two components "into association with" each other, we include that the two components of the kit of parts may be:

(i) provided as separate formulations (i.e. independently of one another), which are subsequently brought together for use in conjunction with each other in combination therapy; or (ii) packaged and presented together as separate components of a "combination pack" for use in conjunction with each other in combination therapy.

Compounds of the invention may be administered at varying doses. For e.g. parenteral (e.g intravenous) doses, a suitable interval is about 0.2 to 200 mg per kg body weight, such as about 20 to 100 mg per kg body weight. Doses may be given continuously or in divided doses once, twice, three or four times or more daily.

In any event, the physician, or the skilled person, will be able to determine the actual dosage which will be most suitable for an individual patient, which is likely to vary with the route of administration, the type and severity of the condition that is to be treated, as well as the species, age, weight, sex, renal function, hepatic function and response of the particular patient to be treated. The above-mentioned dosages are exemplary of the average case; there can, of course, be individual instances where higher or lower dosage ranges are merited, and such are within the scope of this invention.

Compounds of the invention have the advantage that they are capable of blocking the action of 3-alpha-hydroxy-pregnan-steroids on the human $GABA_A$ receptor.

The term "blocking" is employed in this context to define an effect where the 3-alpha-hydroxy-5-alpha/beta-steroids are prevented by a compound of the invention from acting on the GABA-R receptor. "Blocking" is thus a different term to what is normally meant by "modulation" or "repression" or similar terms, which suggest that pharmacological action is still taking place, but to a lesser extent or at a slower rate. In this way, an "antagonist" means a substance that hinders another substance, e.g. an agonist, to induce its effect. In this application the terms "antagonist" and "blocker" may be used interchangeably.

As discussed hereinbefore, compounds of the invention also have the advantage that they selectively block the action of 3-alpha-hydroxy-5alpha/beta-pregnan-steroids on the $GABA_A$ receptor by simultaneous administration, with only limited effects on (at most partial antagonists of) the GABA effect.

In addition to the advantages mentioned hereinbefore, compounds of the invention may further have the advantage that they may be more efficacious than, be less toxic than, be longer acting than, be more potent than, produce fewer side effects than, be more easily absorbed than, and/or have a better pharmacokinetic profile (e.g. higher bioavailability, resulting for example from an improved solubility in aqueous solvents, and/or lower clearance) than, and/or have other useful pharmacological, physical, or chemical properties over, compounds known in the prior art, whether for use in the above-stated indications or otherwise.

Whenever the term "about" is employed herein, for example in the context of amounts (e.g. doses of active ingredients), or time periods, it will be appreciated that such variables are approximate and as such may vary by ±10%, for example ±5% and preferably ±2% (e.g. ±1%) from the numbers specified herein.

The invention is illustrated, but in no way limited, by the following examples.

EXAMPLE 1

Synthesis of 3α-ethynyl, 3β-hydroxy, 5α-pregnan-20-oxime

It has been identified that a reaction of the ethynyl Grignard reagent with 3, 20/17 diketone steroids is in most cases selective for the position 3 and no need for protection/deprotection for the other ketone functionality is required. Both alpha and beta isomers are formed, which can be separated by chromatographic methods and recrystallized.

Starting materials for synthesizing 3α-ethynyl, 3β-hydroxy, 5α-pregnan-20-oxime are the corresponding steroids with 3-hydroxyl substituent and keto group in positions 20. They can be converted to the respective diones by oxidation with IBX reagent. The reaction proceeds smoothly and with complete conversion. Other opportune steroids can be employed as starting material when required. The reactions were carried out in opportune solvents such as methanol, ethanol, water, THF, diethyl ether, dichloromethane or other solvents that one skilled in the art can recognize as opportune. The reactants are chosen in order to avoid, when possible, use of reactants, such as heavy metals, which are toxic even in traces or are difficult to be completely removed in the workup procedure.

Reactions involving air or moisture sensitive reagents or products were carried out under inert atmosphere, such as nitrogen or argon gas, in the presence of dry solvents. Diethyl ether and tetrahydrofuran were dried over Na in the presence of benzophenone. Syringes purged with inert gas were used for the transfer of reagents and dry solvents. Optimized time and temperature of the reactions were determined by monitoring the formation of products and the loss of starting material using a suitable chromatographic technique such as TLC or GC/MS.

Purifications were carried out by using chromatographic techniques such as flash silica chromatography or preparative high performance liquid chromatography (HPLC) by using a HPLC apparatus. Those skilled in the art can recognize that alternative purification methods can be employed, and laboratory chromatographic techniques can be adapted to industrial scale by using chromatographic columns for scaled preparations. Identification of the products are carried out by using suitable analytical techniques such as 1H-NMR, 13C-NMR, mass spectrometry, IR spectroscopy, X-ray spectroscopy and any other assay that one skilled in the art can recognize as opportune for structural identification and purity determination of 3α-ethynyl, 3β-hydroxy, 5α-pregnan-20-oxime. One skilled in the art will recognize that similar reagents, solvents, conditions and parameters can be used in the reactions, depending on the substrate. NMR data are recorded using a Bruker 400 MHz spectrometer.

3α-ethynyl, 3β-hydroxy, 5α-pregnan-20-one 3,20-5α-pregnandione (1.580 g, 5.0 mmol) was dissolved in 50 mL dry THF at room temperature (rt) under nitrogen. Ethynyl magnesium bromide (1.1 equiv) was added dropwise at rt under stirring and the solution was left stirring overnight at rt under nitrogen flow.

The yellowish solution was then quenched with saturated $NH_4Cl_{(aq)}$ and the aqueous phase extracted with dichloromethane (3×30 mL). The collected organic phases were evaporated under reduced pressure, the resulting yellow oil dissolved in dichloromethane, washed with brine and dried over $MgSO_4$. The solution was reduced under vacuum, and the residue purified by silica flash column chromatography (1:4 diethylether:dichloromethane). Typical yields were 72%. Eventual traces of by products may be eliminated by further recrystallization from diethylether.

$^1$H NMR (400 MHz, $CDCl_3$-$d_6$): δ 2.51 (t, 1H); 2.47 (s, 3H); 2.14 (m, 1H); 2.11 (s, 3H); 0.81(s, 1H); 0.60 (s, 3H).

3α-ethynyl, 3β-hydroxy, 5α-pregnan-20-one

This compound was obtained as by product from the above described reaction and separated by silica flash column chromatography. Typical yield was 13%.

$^1$H NMR (400 MHz, $CDCl_3$-$d_6$): δ 2.52 (t, 1H); 2.43 (s, 1H); 2.11 (s, 3H); 0.80 (s, 3H), 0.60 (s, 3H).

3α-ethynyl, 3β-hydroxy, 5α-pregnan-20-oxime

3α-ethynyl, 3β-hydroxy, 5α-pregnan-20-one (10 mmol) was dissolved in dichloromethane 5 mL and ethanol 50 mL at rt and air atmosphere, in a 250 mL round bottom flask. 4 equiv. of $NH_2OH$ chlorhydrate and 4 equiv. of sodium acetate were dissolved in 5 mL $H_2O$ and then added to the steroid solution. 20 mL of ethanol was added and the mixture put on reflux overnight. The mixture was then cooled and the solvent removed under reduced pressure. The white residue was then treated with 50 mL $H_2O$ and 50 mL dichloromethane, the aqueous phase extracted with 3×30 mL dichloromethane. The collected organic phases were then dried over $MgSO_4$, filtrated and the solvent removed under reduced pressure. The final residue was purified by silica flash column chromatography dichloromethane:diethyl ether 4:1, typical yields 95-100%.

$^1$H NMR (400 MHz, $CDCl_3$-$d_6$): δ 2.47 (s, 1H); 2.22 (t, 1H); 2.05 (m, 1H); 1.88 (s, 3H); 1.86 (m, 1H); 0.81 (s, 3H), 0.62 (s, 3H).

EXAMPLE 2

Effects of 3α-ethynyl, 3β-hydroxy, 5α-pregnan-20-oxime on $GABA_A$ Receptor Subtype Alpha 5 and Alpha 1

HEK-293 cells, permanently transfected with the human α1β2γ2 $GABA_A$ and α5β3γ2 $GABA_A$ receptor expressing functional α1β2γ2L and α5β3γ2L $GABA_A$ receptors were used. The cell lines permanently expressing a functional human $GABA_A$ receptor was made in following steps. The $GABA_A$ receptor subunits α1(308-1727 NM_000806), β2 (214-1679 NM_000813), and γ2L (290-1785 NM_198904) including introduced Kozac sequences just before the start codons were subcloned into mammalian expression vectors containing Geneticin, Hygromycin B, and Zeocin resistance, respectively. A HEK-293 cell line stably expressing the three $GABA_A$ receptor subunits was produced by transfection of the subunits one at a time. The transfection was followed by selection with the appropriate antibiotics, cell separation with the use of subunit specific antibodies (β2 and γ2), and production of single cell colonies. Produced cell lines were analysed with immunocytochemistry for the three $GABA_A$ receptor subunits, followed by selection of a suitable cell line showing for the $GABA_A$ receptor normal and good reactivity in a patch-clamp analysis (see below) towards GABA and the GAMS tetrahydrodeoxycorticosterone (TH-DOC).

Methods for Testing $GABA_A$ Receptor Effects of 3α-ethynyl, 3β-hydroxy, 5α-pregnan-20-oxime Experiments were carried out to investigate the effect of 3α-ethynyl, 3β-hydroxy, 5α-pregnan-20-oxime on the $GABA_A$ receptor function in absence and in presence of the GAMS Tetrahydrodeoxycorticosterone (THDOC) by the Dynaflow™ system on HEK-293 cells. In these tests the protocol was optimized to be similar to the physiological conditions in the synaptic cleft.

Cell culture: HEK-293 cells, permanently transfected with human α1β2γ2 $GABA_A$ and α5β3γ2 $GABA_A$ receptor subtypes, were seeded at a density of $3×10^4/25$ $cm^2$ in cellbind culture flask. The transfected cells were used for patch-clamp experiments 3 days after seeding. When using the cells for patch-clamp experiments the cells were washed twice with $O_2$ bubbled EC-solution (see below). About 5 mL EC was then added and the cells were kept in the incubator for about 15 minutes. After 15 minutes the cells come loose from the bottom of the flask and were separated by carefully sucking couple of times with a Pasteur pipette.

Dynaflow™ system: Dynaflow™ system with resolve chips was used for all patch-clamp experiments. The resolve chips is made of non-sticky materials. The channel width is 150 μm and the height 50 μm. The well volume is 280 μL. Run time at the flow rate of 26 μL/min. is 180 min. The pump settings were as follow: Omnifix 2 mL syringe with inner diameter of 9.65 mm was used. The syringe pump flow rate of chip was 26 μL/min.

Steroids and GABA: GABA was dissolved in EC-solution by ultrasound for about 40 minutes to the concentration of 10 mM in room temperature. All steroids were dissolved to the concentration of 6 mM in ethanol. The ethanol concentration was 0.1% in all end-solutions, including the wash solution (EC) and the solution with GABA alone. End-solutions are the solutions added into the wells of the chip.

Electrophysiology: Patch electrodes were pulled from 1.5 mm O.D., 0.86 mm I.D. borosilicate capillary glass without filament. Typical electrodes had a resistance of 2-5 MΩ when filled with intracellular solutions. The intracellular solution consisted of (in mM): 140 Cs-gluconate, 3.0 NaCl, 1.2 $MgCl_2$, 1.0 EGTA, 10 HEPES. pH was adjusted to 7.2 with CsOH. The extracellular (EC) solution used during recordings contained (in mM): 137 NaCl, 5.0 KCl, 1.0 CaCl2, 1.2 $MgCl_2$, 10 HEPES, 10 glucose. pH was adjusted with NaOH to 7.4. After compensating for the liquid junction potential a steady holding potential of −17 mV was used in all experiments. In physiological conditions the HEK-293 has a resting potential at −40 mV and a low concentration of chloride ions inside the cell. By using the holding potential of −17 mV and the intracellular solution with low chloride ion concentration the chloride ions flux into the cell when the receptors are activated. All experiments were performed at room temperature (21 to 23° C.). A standard protocol was used for all experiments.

Protocol

GABA applications: By using the Dynaflow equipment it is possible to study transfected HEK-293 during almost physiological conditions. The Dynaflow system allows application of solutions for as short as 40 ms up to minutes in time. Physiologically, in the synaptic cleft, GABA is released in mM range for about 2 ms this is valid for alpha1 receptors. In extra synaptic sites the GABA levels are lower but stay on for longer time this is valid for the alpha5 receptors. In experiments with α1β2γ2L we have applied GABA±steroid for 40 ms; in experiments with α5β3γ2L, GABA±steroid was applied for 6 s. It was found that in almost all cells, the first GABA application gave a smaller response than the second GABA application. There was no difference in response between the second and the third GABA application. Therefore the first GABA application is always repeated twice and the second response is used in the analysis.

Washout: GABA is quite soluble in water and easy to washout from the receptor. The washout time was set to 1 minute after application with GABA solely. Steroids on the other hand are difficult to dissolve in water and also difficult to washout from the receptor. In our experiments, we used THDOC as the GABA agonist. With 2 minutes washout time, 200 nM THDOC had been completely washed out as shown by neither an accumulative nor a desensitization effect.

Incubation: To see the effect of the steroids and to achieve stable results we found out that the steroids have to be incubated on the receptor before application of GABA. This finding is supported by the suggestion that the binding site for THDOC is located intracellular on the receptor (Hosie et al 2006). Different incubation times were studied to achieve the optimal time for attain stable results and minimize the washout time. Incubation time of 20 seconds showed to be the optimal time for washout time of 2 minutes.

Conclusion of optimization: The optimized protocol is like follow: 20 seconds incubation of steroids, 40 ms or 6 s. GABA±steroids application, 2 minute washout. The first GABA application is repeated twice with a washout time of 1 min. between the first and the second application.

Results of testing 3α-ethynyl, 3β-hydroxy, 5α-pregnan-20-oxime on $GABA_A$ receptor α1β2γ2L and α5β3γ2

The results of the patch clamp testing of 3α-ethynyl, 3β-hydroxy, 5α-pregnan-20-oxime in the two different $GABA_A$ receptor subtypes α1β2γ2L and α5β3γ2L gave an unexpected and surprising result. As shown in Table 2, 3α-ethynyl, 3β-hydroxy, 5α-pregnan-20-oxime had, in the α1β2γ2L receptor, no antagonistic effect against the enhancing effect of THDOC, the GAMS used in the experiments. 3α-ethynyl, 3β-hydroxy, 5α-pregnan-20-oxime alone had no enhancing or antagonizing effect on chloride flux. 3α-ethynyl, 3β-hydroxy, 5α-pregnan-20-oxime had a slight agonistic effect on GABA's opening of the α1β2γ2L $GABA_A$ receptor. This agonistic effect is so small that it has no relevance and in the range of the vehicle.

Surprisingly, on the α5β3γ2L receptor subtype 3α-ethynyl, 3β-hydroxy, 5α-pregnan-20-oxime is an antagonist in all tested situations with GAMS and GABA (Table 2). 3α-ethynyl, 3β-hydroxy, 5α-pregnan-20-oxime, thus show specificity depending on the receptor subtype. 3α-ethynyl, 3β-hydroxy, 5α-pregnan-20-oxime is therefore showing selectivity in its action and therefore suitable as a medication. As 3α-ethynyl, 3β-hydroxy, 5α-pregnan-20-oxime is specific and not active on the α1β2γ2L receptor, 3α-ethynyl, 3β-hydroxy, 5α-pregnan-20-oxime will have less side effects due to the more general alpha1 receptor. The inhibition of the effect as an antagonist gives a greater impact than a similar positive change as an agonist.

TABLE 2

Studies on current response mediated by chloride ion flux through the $GABA_A$ receptors expressing the α1 and α5 subunit. Patch clamp technique combined with the Dynaflow ™ application system, which provides rapid applications of and removal of substances, was used in this study. "Compound" refers to 3α-ethynyl, 3β-hydroxy, 5α-pregnan-20-oxime. "GAMS" refers to "$GABA_A$ receptor modulating steroids" in this case tetrahydrodeoxycorticosterone (THDOC).

| $GABA_A$ receptor subtype | Compound + GAMS + GABA | Compound alone | Compound + GAMS | Compound + GABA |
|---|---|---|---|---|
| α1β2γ2L | No effect | No effect | N.D. | +11 ± 4 |
| α5β3γ2 | −15.2 ± 2.8 | No effect | −29.7 ± 6.5 | −18.8 ± 2.2 |

α1β2γ2-$GABA_A$ Receptors

1 μM 3α-ethynyl, 3β-hydroxy, 5α-pregnan-20-oxime increased the GABA mediated current response on α1β2γ2L-$GABA_A$ receptors by approximately 10% (Table 2). 1 μM 3α-ethynyl, 3β-hydroxy, 5α-pregnan-20-oxime did not activate the $GABA_A$ receptor directly, in absence of GABA. The results from this study show that 3α-ethynyl, 3β-hydroxy, 5α-pregnan-20-oxime does not modulate GABA evoked currents negatively at α1β2γ2-$GABA_A$ receptors. Furthermore, the observed 10% increase of the GABA evoked currents at the α1-subunit type must be considered a minor effect. In summary, 3α-ethynyl, 3β-hydroxy, 5α-pregnan-20-oxime does not have any major effects on GABA evoked currents at the α1β2γ2L-$GABA_A$ receptors.

α5β3γ2-$GABA_A$ Receptors

A clear concentration dependent antagonizing effect was detected for 3α-ethynyl, 3β-hydroxy, 5α-pregnan-20-oxime on the 200 nM GAMS (THDOC) and 0.3 μM GABA evoked currents (Table 3). 3α-ethynyl, 3β-hydroxy, 5α-pregnan-20-oxime also had an antagonizing effect on the 200 nM THDOC evoked current, i.e. the direct activation of the $GABA_A$ receptor by GAMS. This antagonism had the same magnitude as the one on the 200 nM THDOC and 0.3 μM GABA evoked current.

TABLE 3

0.1-3 μM 3α-ethynyl, 3β-hydroxy, 5α-pregnan-20-oxime ("Compound") in presence of 200 nM THDOC + 0.3 μM GABA. Relative effect to control 200 nM THDOC + 0.3 μM GABA, set to 0.

| Dose Compound μM | Relative effect Mean (%) | Median | SEM | n | Min. | Max. | P-value |
|---|---|---|---|---|---|---|---|
| 0.1 | −3.0 | −1.6 | 2.0 | 10 | −19.6 | 2.8 | 0.093 |
| 0.3 | −6.6 | −6.9 | 3.2 | 10 | −22.8 | 6.0 | 0.114 |
| 1 | −15.2 | −11.0 | 2.8 | 11 | −30.0 | −2.5 | 0.003 |
| 3 | −20.7 | −23.6 | 2.3 | 9 | −30.0 | −10.4 | 0.008 |

EXAMPLE 3

Comparative Effects of 3α-ethynyl, 3β-hydroxy, 5α-pregnan-20-oxime and its Epimer on $GABA_A$ Receptor Subtype Alpha 5

By employing the procedures described in Example 2 above, 3α-ethynyl, 3β-hydroxy,5α-pregnan-20-oxime and its epimer, 3β-ethynyl, 3α-hydroxy, 5α-pregnan-20-oxime were tested for effects on $GABA_A$ receptor subtype alpha 5.

The only methodological difference in the procedures employed compared to Example 2 was that steroids were dissolved in ethanol to a concentration of 2 mM in the stock solution, with a final ethanol concentration of 0.1% in all solutions. The results are tabulated in Table 4 below.

TABLE 4

Effects of tested UC-steroids 3α-ethynyl, 3β-hydroxy, 5α-pregnan-20-oxime ("Compound") and 3β-ethynyl, 3α-hydroxy, 5α-pregnan-20-oxime ("Comparator") in concentrations of 1 μM tested against the GABA-steroid THDOC measured as change in chloride flow through the α5β3γ2L GABA$_A$ receptor.

| Steroid | Mean % (SEM) Compound + THDOC + GABA | Mean % (SEM) Compound + THDOC | Mean % (SEM) Compound + GABA | Mean % (SEM) Compound alone |
|---|---|---|---|---|
| Compound | −15 (3) antagonist | −30 (6) antagonist | −19 (2) antagonist | no effect |
| Comparator | +80 (8) agonist | +128 (22) agonist | +210 (23) agonist | +50 (12) agonist |

The results show that the compound of the invention acts as an antagonist of the GABA receptor subunit alpha 5, whereas the epimer acts as an agonist.

The invention claimed is:

1. 3α-ethynyl, 3β-hydroxy, 5α-pregnan-20-oxime or a pharmaceutically acceptable salt thereof.

2. A pharmaceutical formulation comprising a compound as defined in claim 1, in admixture with a pharmaceutically acceptable adjuvant, diluent or carrier.

3. A combination product comprising:
   (A) a compound as defined in claim 1; and
   (B) at least one other therapeutic agent that is useful in the treatment of a steroid-related CNS disorder,
   wherein each of components (A) and (B) is formulated in admixture with a pharmaceutically-acceptable adjuvant, diluent or carrier.

4. A combination product which comprises a pharmaceutical formulation including a compound as defined in claim 1, at least one other therapeutic agent that is useful in the treatment of a steroid-related CNS disorder, and a pharmaceutically-acceptable adjuvant, diluent or carrier.

5. A combination product which comprises a kit of parts comprising components:
   (a) a pharmaceutical formulation comprising a compound of formula I as defined in claim 1, in admixture with a pharmaceutically-acceptable adjuvant, diluent or carrier; and
   (b) a pharmaceutical formulation comprising at least one other therapeutic agent that is useful in the treatment of a steroid-related CNS disorder in admixture with a pharmaceutically-acceptable adjuvant, diluent or carrier,
   which components (a) and (b) are each provided in a form that is suitable for administration in conjunction with the other.

6. A process for the preparation of a compound of formula I as defined in claim 1, which process comprises reaction of 3α-ethynyl, 3β-hydroxy, 5α-pregnan-20-one with hydroxylamine.

7. A process for the preparation of a pharmaceutical formulation as defined in claim 2, which process comprises bringing into association 3α-ethynyl, 3β-hydroxy, 5α-pregnan-20-oxime with a pharmaceutically-acceptable adjuvant, diluent or carrier.

8. A process for the preparation of a combination product as defined in claim 3, which process comprises bringing into association 3α-ethynyl, 3β-hydroxy, 5α-pregnan-20-oxime with the other therapeutic agent that is useful in the treatment of a steroid-related CNS disorder, and at least one pharmaceutically-acceptable adjuvant, diluent or carrier.

* * * * *

UNITED STATES PATENT AND TRADEMARK OFFICE
CERTIFICATE OF CORRECTION

PATENT NO. : 10,351,589 B2
APPLICATION NO. : 15/542800
DATED : July 16, 2019
INVENTOR(S) : Torbjorn Backstrom et al.

Page 1 of 1

It is certified that error appears in the above-identified patent and that said Letters Patent is hereby corrected as shown below:

In the Claims

At Column 10, Claim number 5, Line number 10, delete "of formula I";

At Column 10, Claim number 6, Line numbers 22 and 23, delete "of formula I".

Signed and Sealed this
Twenty-second Day of October, 2019

Andrei Iancu
*Director of the United States Patent and Trademark Office*